US008066632B2

(12) United States Patent  
Dario et al.

(10) Patent No.: US 8,066,632 B2
(45) Date of Patent: Nov. 29, 2011

(54) TELEOPERATED ENDOSCOPIC CAPSULE EQUIPPED WITH ACTIVE LOCOMOTION SYSTEM

(75) Inventors: Paolo Dario, Leghorn (IT); Arianna Menciassi, Pontedera (IT); Cesare Stefanini, Cascina (IT); Samuele Gorini, Montecalvoli (IT); Giuseppe Pernorio, Pia (IT); Dino Accoto, Andrano (IT)

(73) Assignee: Korea Institute of Science and Technology, Seoul (KR)

( * ) Notice: Subject to any disclaimer, the term of this patent is extended or adjusted under 35 U.S.C. 154(b) by 1191 days.

(21) Appl. No.: 10/598,043

(22) PCT Filed: Feb. 17, 2005

(86) PCT No.: PCT/IB2005/000398
§ 371 (c)(1),
(2), (4) Date: Jun. 25, 2007

(87) PCT Pub. No.: WO2005/082248
PCT Pub. Date: Sep. 9, 2005

(65) Prior Publication Data
US 2008/0091070 A1    Apr. 17, 2008

(30) Foreign Application Priority Data
Feb. 17, 2004 (IT) .............................. PI2004A0008

(51) Int. Cl.
*A61B 1/00* (2006.01)
*A61B 1/04* (2006.01)
(52) U.S. Cl. ..................................................... 600/118

(58) Field of Classification Search ............... 600/101, 600/103, 114, 118, 143
See application file for complete search history.

(56) References Cited

U.S. PATENT DOCUMENTS

| 5,604,531 | A | 2/1997 | Iddan et al. | |
| 5,662,587 | A * | 9/1997 | Grundfest et al. | 600/114 |
| 6,162,171 | A * | 12/2000 | Ng et al. | 600/141 |
| 6,240,312 | B1 | 5/2001 | Alfano et al. | |
| 6,824,508 | B2 * | 11/2004 | Kim et al. | 600/101 |
| 2002/0042562 | A1 * | 4/2002 | Meron et al. | 600/361 |
| 2002/0171385 | A1 | 11/2002 | Kim et al. | |
| 2002/0173700 | A1 * | 11/2002 | Kim et al. | 600/114 |
| 2002/0198470 | A1 * | 12/2002 | Imran et al. | 600/587 |

(Continued)

FOREIGN PATENT DOCUMENTS

JP    04-144533    5/1992

(Continued)

OTHER PUBLICATIONS

International Search Report, dated Jun. 10, 2005, for PCT Application PCT/IB2005/000398.

*Primary Examiner* — Philip Smith
(74) *Attorney, Agent, or Firm* — Sheridan Ross, P.C.

(57) ABSTRACT

A teleoperated endoscopic capsule for diagnostic and therapeutic purposes inside an animal body cavity, comprising a body (1) with a plurality of locomotion modules (5) placed on its surface, suitable for moving said body in the body cavity. The capsule also comprises an energy source inside said body and a microcontroller in the body (1) for actuating the locomotion modules (5) on the basis of commands teletransmitted by an operator. A video camera is then provided for capturing images controlled by said microcontroller and a transceiver system for receiving the commands teletransmitted by the operator and for transmitting the images gained through the video camera.

19 Claims, 4 Drawing Sheets

U.S. PATENT DOCUMENTS

| | | | |
|---|---|---|---|
| 2003/0018280 A1* | 1/2003 | Lewkowicz et al. | 600/549 |
| 2003/0092964 A1* | 5/2003 | Kim et al. | 600/101 |
| 2003/0208107 A1* | 11/2003 | Refael | 600/300 |
| 2003/0216622 A1* | 11/2003 | Meron et al. | 600/300 |
| 2004/0030454 A1* | 2/2004 | Kim et al. | 700/245 |
| 2006/0167339 A1* | 7/2006 | Gilad et al. | 600/101 |

FOREIGN PATENT DOCUMENTS

| | | |
|---|---|---|
| JP | 02-060326 | 8/1993 |
| JP | 05-212093 | 8/1993 |
| JP | 06-054835 | 3/1994 |
| JP | 06-063030 | 3/1994 |
| JP | 06-114036 | 4/1994 |
| JP | 07-156843 | 6/1995 |
| JP | 10-192224 | 7/1998 |
| JP | 2001-071284 | 3/2001 |
| JP | 2001-275926 | 10/2001 |
| JP | 2003-526413 | 9/2003 |
| JP | 2004-000440 | 1/2004 |
| JP | 2005-523101 | 8/2005 |
| JP | 2005-532184 | 10/2005 |
| WO | WO 02/068035 | 9/2002 |
| WO | 03/090618 | 11/2003 |

\* cited by examiner

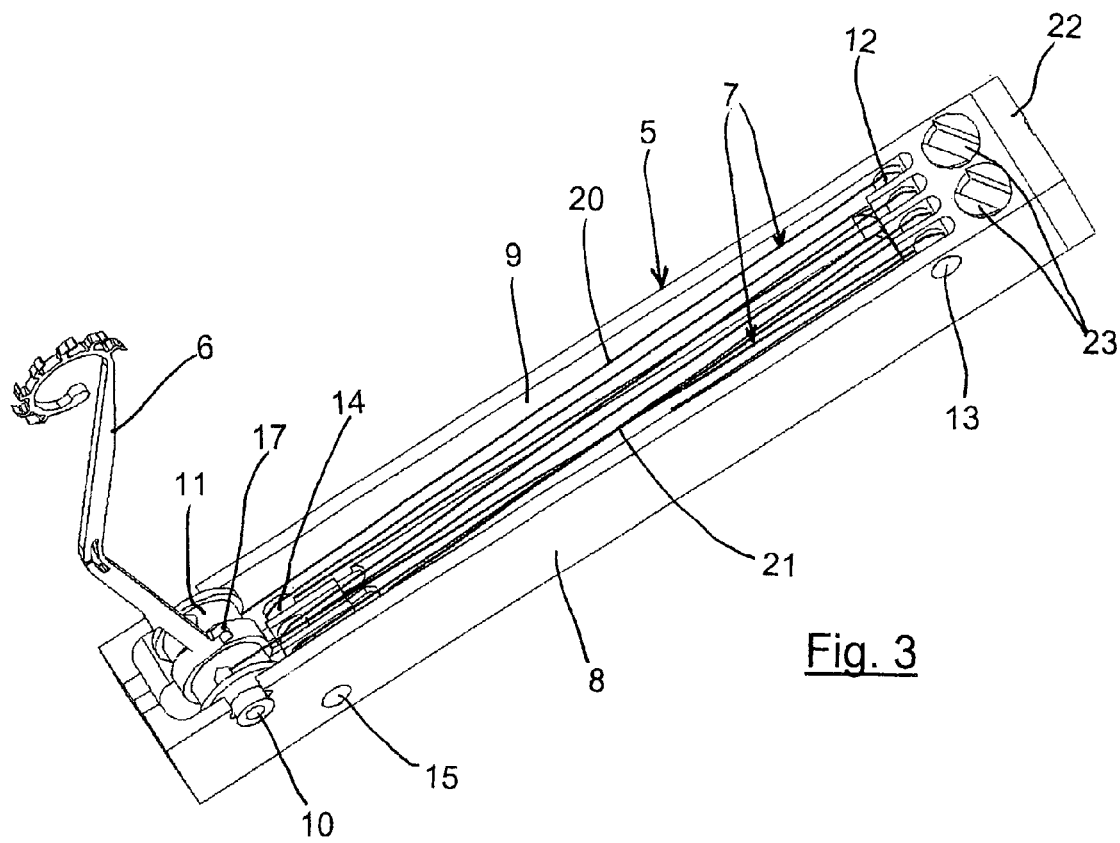
Fig. 3
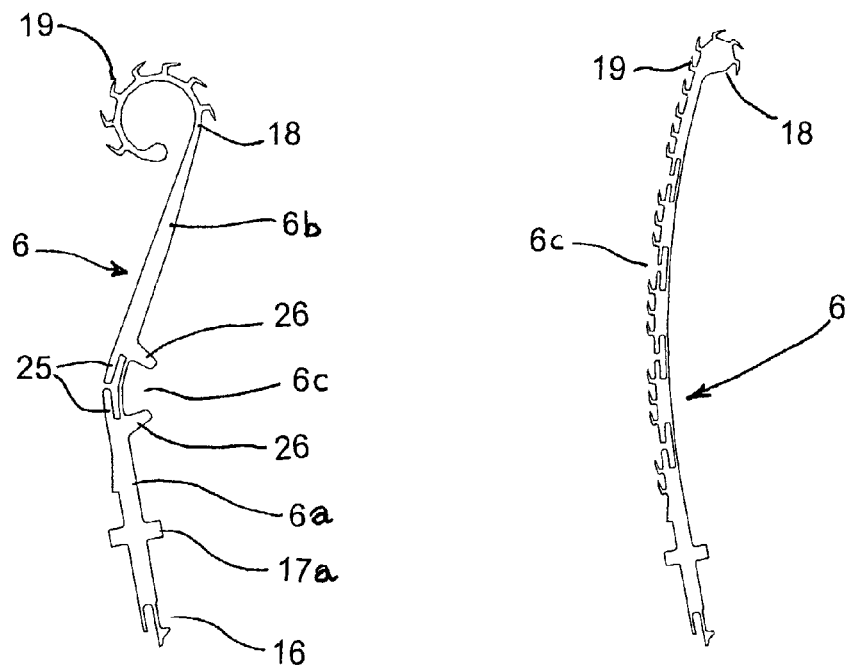
Fig. 4
Fig. 5

TELEOPERATED ENDOSCOPIC CAPSULE EQUIPPED WITH ACTIVE LOCOMOTION SYSTEM

CROSS REFERENCE TO RELATED APPLICATION

This application is a national stage application under 35 U.S.C. 371 of PCT Application No. PCT/IB2005/000398 having an international filing date of Feb. 17, 2005, which designated the United States, which PCT application claimed the benefit of Italian Application Serial No. PI2004A000008, filed Feb. 17, 2004, the entire disclosure of which are hereby incorporated herein by reference.

FIELD OF THE INVENTION

The present invention refers in general to the area of devices for endoscopic use and more specifically relates to a teleoperated endoscopic capsule able to move autonomously in various areas of the human body and in particular in the gastrointestinal tract, with an active control of its locomotion.

DESCRIPTION OF THE STATE OF THE ART

In recent years interest in devices which enable endoscopic investigations and treatments to be performed autonomously and in a minimally invasive way has grown considerably. An autonomous image vision system with wireless data transmission, integrated in a small pill, received recently the approval for clinical evaluation in the US. The system comprises a CMOS imager, a transmitter, LEDs for illumination and a power supply from watch-like batteries. See for example U.S. Pat. No. 5,604,531. The main limitation of this device relates to the lack of active control of the locomotion: the capsule proceeds by normal peristalsis and it cannot be stopped during its journey. Semiautomatic solutions are also known, based on a so-called "inchworm" model of locomotion, such as for example the endoscopic device described in WO02/68035. These systems have limited control potential of the locomotion parameters and no possibility of varying their speed. They also have the disadvantage of sliding with their body along the walls of the body cavity in which they move without being able to avoid any injuries or pathologic areas.

Endoscopic devices are also known which are operated from the outside by means of fields of force (for example magnetic fields) which require the patient to wear suitable apparatus for generation of the field. Refer for example to the device known as Norika 3, produced by the Japanese firm RF System Lab. However use of this device may be awkward and risky due to the possible interferences with other biomedical devices which may be used by the patient. Moreover endoscopic devices with external operation of this type entail the risk of side effects due to prolonged exposure to electromagnetic fields.

OBJECTS AND SUMMARY OF THE INVENTION

The object of the present invention is to provide a device for endoscopic use capable of autonomous movement and power supply within a body cavity, with the possibility of controlling its movements from the outside so as to allow the performance of medical, diagnostic and therapeutic procedures and in particular for transmitting images of areas of interest of the body cavity traversed.

Another object of the present invention is to provide a device for endoscopic use of the type mentioned above with such dimensions as to be able to be swallowed and which is adaptable to the locomotion environment, with the possibility of being stopped, rotated, accelerated and decelerated as required as a result of commands teletransmitted from the outside.

A further object of the present invention is to provide a device for endoscopic use of the type mentioned above provided with legs with several degrees of freedom which can extend radially therefrom and permit locomotion and adaptation thereof to the various shapes of the body area covered, without damaging the tissue with which they come into contact.

Yet a further object of the present invention is to provide a system for endoscopy within a human body cavity which allows an operator to control the locomotion of a teleoperated endoscopic capsule equipped with its own locomotion means, swallowed by a patient, and the reception of images and data acquired thereby.

These objects are achieved with the endoscopic capsule according to the invention, whose basic features are disclosed in claim 1. Further important features are given in the dependent claims.

According to the invention, a teleoperated endoscopic capsule is provided for diagnostic and therapeutic purposes inside a human body cavity, comprising a body with a plurality of locomotion modules on its surface, suitable for moving it inside the body cavity, an energy source and a microcontroller inside said body for actuating said locomotion modules on the basis of commands teletransmitted by an operator, a video camera for capturing images, controlled by the microcontroller, and a transceiver system for receiving the commands teletransmitted by the operator and for transmitting the images acquired via the video camera.

In a particularly preferred embodiment of the invention, the capsule is provided with legs able to extend radially from its body and having at least two degrees of freedom, of which one is active, to allow their movement from a rest position, more particularly situated along the body of the capsule, to a radially extended position, and a passive one for bending the legs around an intermediate portion thereof to adapt them to the deformability of the tissue on which they abut during the movement of the capsule.

Preferably, to operate the movement of the legs actuator means are provided consisting of shape memory alloy (SMA) wires acting, two by two for each leg, in opposition one to the other.

In a particularly preferred embodiment of the invention, the capsule is provided with legs with grasping means, consisting in particular of microhooks at their free ends, to increase friction with the slippery and deformable tissue.

BRIEF DESCRIPTION OF THE DRAWINGS

Further features and advantages of the endoscopic capsule according to the present invention will be made clearer by the following description of one of its embodiments, given by way of a non-limiting example with reference to the accompanying drawings in which:

FIG. 3 is a perspective view of a locomotion module of the endoscopic capsule of FIG. 1;

FIG. 4 is a side perspective view of a leg with which the locomotion module of FIG. 3 is equipped;

FIG. 5 is a variant of the leg of FIG. 4;

DETAILED DESCRIPTION OF THE INVENTION

Figure 1:
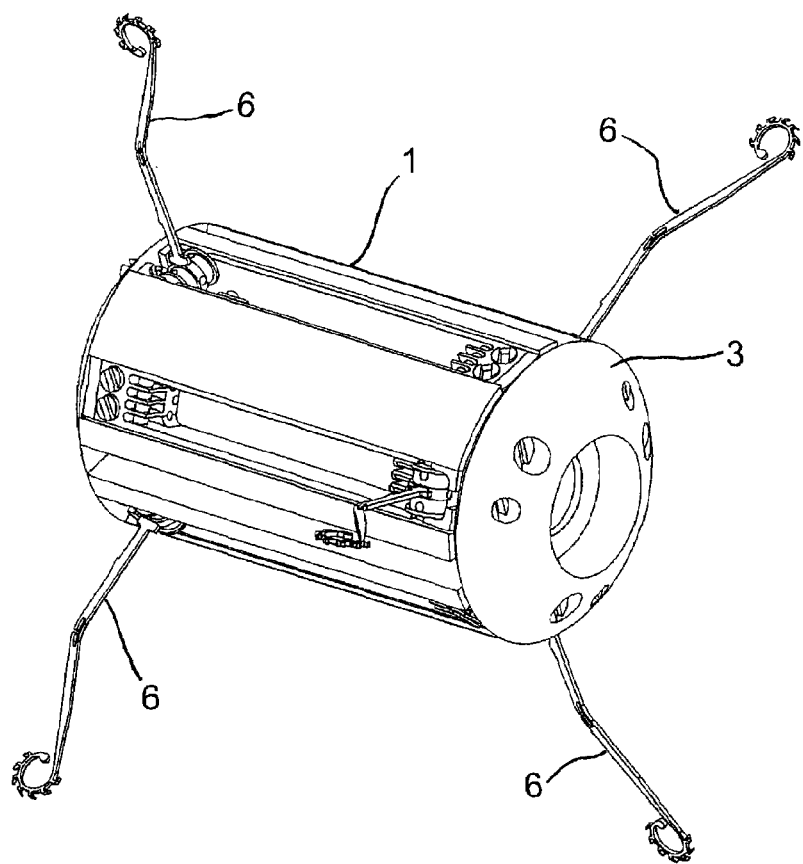
FIG. 1 is a perspective view of the endoscopic capsule according to the invention.
Figure 2:
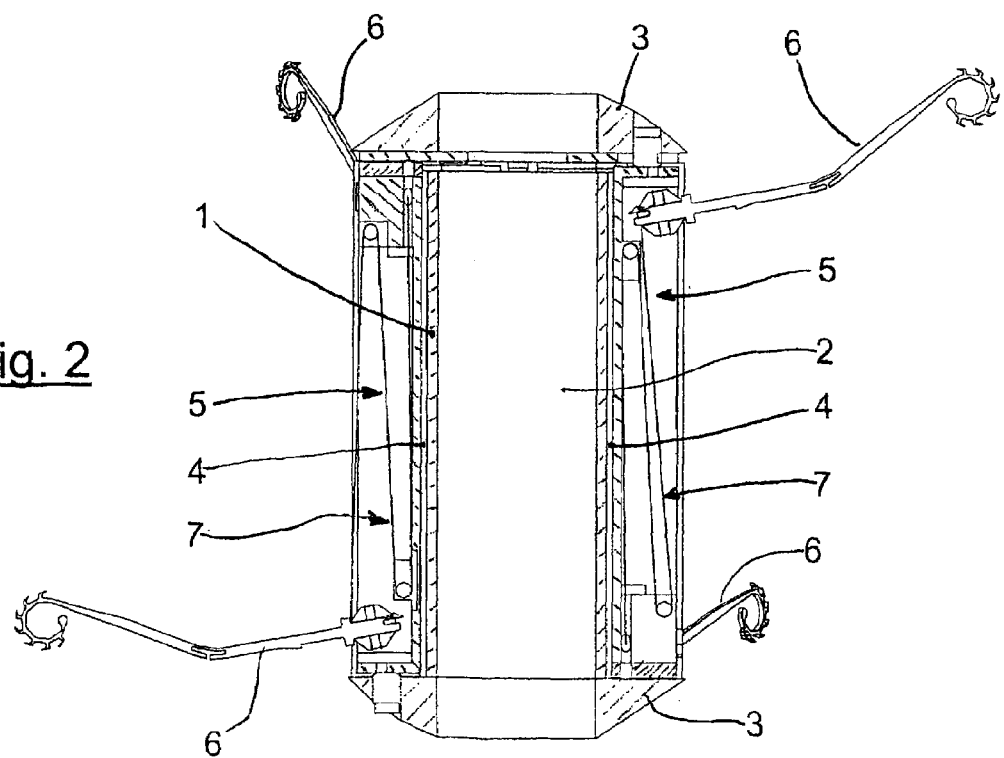
FIG. 2 is an enlarged, axially sectioned view of the endoscopic capsule of FIG. 1.

Referring to FIGS. 1 and 2, the endoscopic capsule according to the invention is formed by a substantially cylindrical body 1, preferably made in a biocompatible plastic material, having a longitudinally spaced front end and rear end and defining an internal chamber 2 for housing a video camera (not shown) for capturing images, electrical power supply and the control electronics, as will be explained herein below. At the ends of the body 1 closure caps 3 are attached and the cap placed at the front end has an aperture for the optical system of the video camera, for the administration of drugs and for the passage of bioptic or surgical instruments.

Along the side surface of the body 1 equally spaced axial grooves 4 are formed (six in the present embodiment of the invention), suitable for housing respective locomotion modules, generically denoted by 5, each one comprising a leg 6 and an actuator unit 7.

More particularly, referring also to FIG. 3, each locomotion module 5 comprises an elongated support 8, of such a size as to be able to be housed in a corresponding groove 4, along which a channel 9 is formed axially. At one end of the channel 9 a pin 10 is placed transversely and a pulley 11 is keyed on the pin 10. The leg 6 extends radially from the pulley 11. At the other end of the channel 9 transmission rollers 12 are placed, freely rotating on a transverse pin 13 integral with the support 8, while additional transmission rollers 14 are provided near the pulley 11 in the seat 9, likewise rotating on a transverse pin 15 attached to the support 8. In a possible embodiment of the invention the pulley 11 is made in aluminium, while the pins 12 and 14 are in a non-conductive material, for example glass.

The locomotion modules 5 are placed on the body 1 in such a way that the legs 6 are alternatively at one and the other end, so that definitively, in the present embodiment of the invention, the capsule is provided with three legs at one end and three legs at the other, spaced angularly through 120° and staggered through 60°.

Referring to FIG. 4, each leg 6 is formed by a rod-shaped element in two portions 6a and 6b connected by a knee portion 6c with increased flexibility. The portion 6a has at its free end a joint 16 for snap connection in a special seat 17 of the pulley 11, and at an intermediate point a retaining shoulder 17a. The portion 6b has a substantially circular end 18 and a plurality of microhooks 19, turned in the same direction extends radially therefrom.

In the currently preferred embodiment of the invention, the leg 6 is made in SMA (Shape Memory Alloy) in a superelastic phase at room temperature. In this way it is possible to exploit the relatively high elasticity of the metal, which allows deformation of up to 8%, much higher than those of a normal metal, together with its mechanical strength and biocompatibility. In this way it is also possible to make the legs 6 via an electro-erosion process from a small plate of this metal alloy.

The leg 6 therefore has two degrees of freedom, of which one is active around the pulley 11, for the movement of the leg in the longitudinal direction, and a passive one around the knee portion 6c to adapt the leg to the deformability of the tissue on which it abuts.

The actuator unit 7 allows angular movements of the leg 6 of a controllable extent between a rest position, wherein the leg 6 is extended longitudinally in the seat 9 of the support 8, and a position of maximum radial extension angularly spaced through 120° in relation to the rest position. The actuator unit 7, shown in particular in FIGS. 2 and 4, is formed, for each leg 6, by a pair of wires 20 and 21 in SMA with one end attached to the pulley 11 at diametrically opposite parts, while the other end is connected to the power supply system via contacts, not shown, provided on a contact plate 22 placed at one end of the support 8, the wires 20 and 21 being coupled to the contact palte 22 by means of attachment dowels 23. The wires 20 and 21 have two transmissions at transmission rollers 12 and 14 in order to maximise the contraction of the metal. Note that in FIG. 2, for each of the two locomotion modules 5 shown sectioned, only one of the two wires 20 and 21 in SMA provided has been drawn for the sake of clarity of illustration.

The two wires 20 and 21 act in opposition. The rotation of the pulley, and hence of the leg 6, is produced by actuating alternately one of the two wires. Actuation is achieved by passing current through one wire and causing its heating to the transition temperature which varies according to the SMA chosen. Having reached the transition temperature the wire contracts suddenly, rotating the pulley, while the cold wire is deformed through the action of the hot wire.

The leg 6 has, at the knee portion 6c, two opposite appendages 25 which limit to a few degrees rotation of the leg 6 in the direction of its elongation, while on the opposite side of the leg 6 an additional pair of appendages 26 can be provided, suitable for abutting one against the other after an extensive, relative rotation of the portion 6b in relation to the portion 6a. The pair of appendages 26 therefore limit the extent of the bending to which the leg 6 may be subjected so as to prevent possible damage.

In the embodiment of FIG. 5, the leg 6 is formed by a rod-shaped element along which a plurality of flexible joints 6c are provided to improve its adaptability to the various conditions encountered along a journey. The leg 6 according to this embodiment also has a plurality of microhooks 19 present not only along the edge of its free end 18, but also along a whole edge of the leg 6 so as to create directional friction along the whole leg and not only at its free end.

The endoscopic capsule according to the invention is able to move, rotate and stop inside a body cavity, such as for example the gastrointestinal (GI) tract, as a result of commands teletransmitted by an outside operator. The capsule is moved forwards by actuating in a synchronised manner the legs 6 whose free ends force against the walls delimiting the body cavity. This forcing action is regulated by the possibility of the leg to deform at its knee portion 6c, reducing the risk of damaging tissue. The microhooks 19 provided at the free end of the legs 6 increase the friction between the ends of the leg and the tissue, friction otherwise very low due to the slippery and deformable nature of the tissue walls involved. The microhooks are turned backwards in relation to the forward movement, i.e. towards the rear end of the body 1, in order to have a differential friction coefficient at the interface required for propulsion of the capsule.

Figure 6:
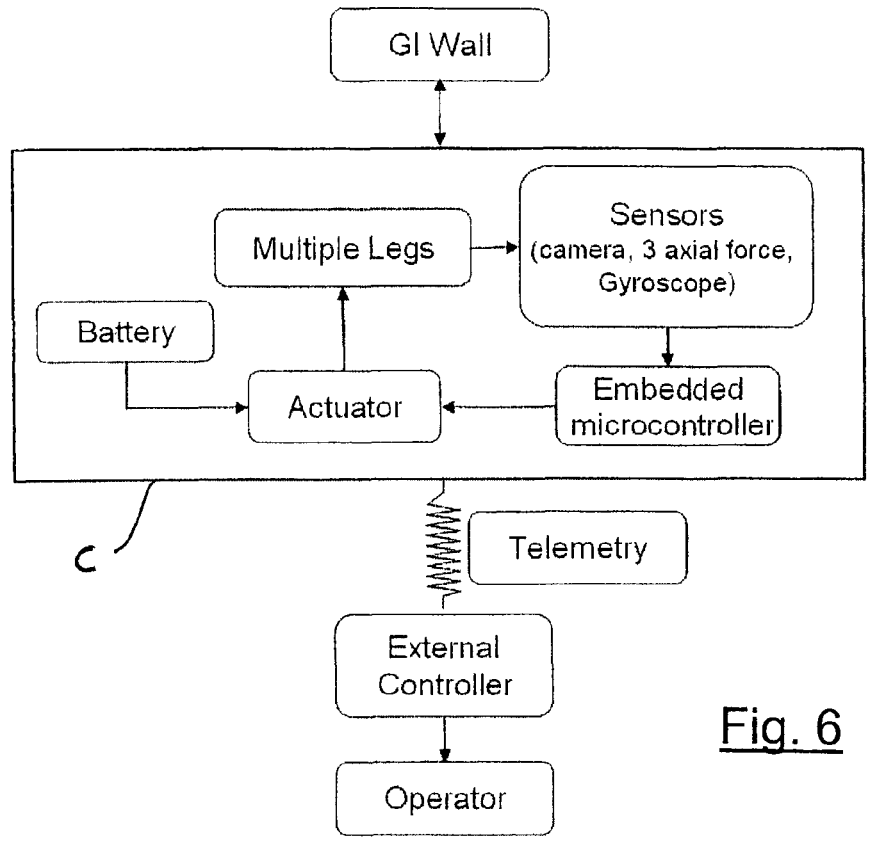
FIG. 6 is a block diagram of the mechatronic architecture for locomotion of the capsule.

FIG. 6 illustrates the overall mechatronic architecture of the system of control of the locomotion of the endoscopic capsule according to the invention. Basically this system is composed of a capsule system, denoted by C, and an external control system, identified by the EXTERNAL CONTROLLER block, which forms the interface with the operator, which transmits the commands to the capsule through this block via a radio signal. The operator selects the commands, such as move forwards, stop, rotate, turn back, and these commands, once transmitted to the capsule, are interpreted by the internal microcontroller into operations of a lower level to activate the of actuation sequence necessary for generating the required command.

Figure 7:
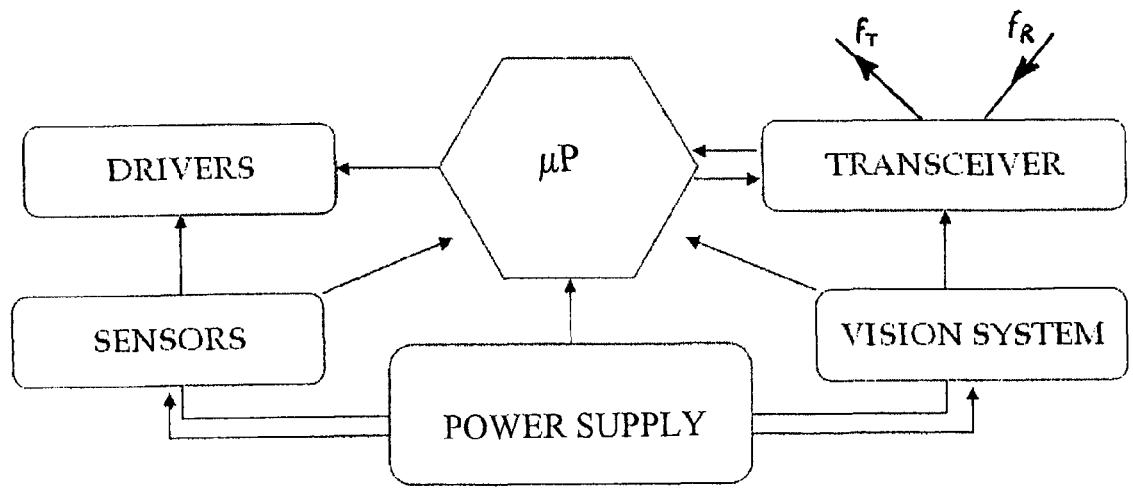
FIG. 7 is a block diagram of the control system on board the capsule.

For actuation of the legs 6 a microcontroller (ÿP) is provided, housed in the body 1 of the capsule for generating a train of pulses according to the Pulse Width Modulation (PWM) technique. As shown in FIG. 7, the microcontroller sends the actuation signals to the drivers of the actuators of the legs 6, whose angle of aperture is monitored via suitable sensors which also allow a closed-cycle control to be carried out. The microcontroller also processes the signals from the vision system and a two-directional data transmission system is provided (TRANSCEIVER block).

The data transmission system is based on transmission in RF and uses commercial systems. The band of transmission used can be that operating in the VHF or UHF field, for example a frequency of 433 MHz could be used. Among the commercial components which can be used, mention is made of those of Microchip, Cypress Microsystem, Chipcon AS SmartRF and others.

The capsule system remains in a standby condition until a command is received from the external controller. Once the signal has been received, the type of command to be performed is identified. The commands to be performed relate both to locomotion and sensor monitoring. In practice, if information is required on the status of the capsule, the microcontroller sends, via the transmission system, the status of the various sensors on board and this allows a reconstruction of the position of the individual legs and to have, for example, information on whether the legs are open or closed. In the case instead of a locomotion command, the microcontroller has to determine which type of locomotion to carry out, that is to say whether to go forwards, backwards, rotate left or right, move one leg only or a subgroup of legs (which occurs in the case of locomotion on areas where it is not necessary to move all the legs but instead just a few are sufficient and this with a view to saving energy). Once the action to be taken has been determined, the microcontroller sends voltage pulses of a value between 3.3V and 5V to the drivers for activation of the actuator. Once the operation has been performed, the microcontroller checks that there are no actions to be performed so as to return to a standby condition.

Figure 8:
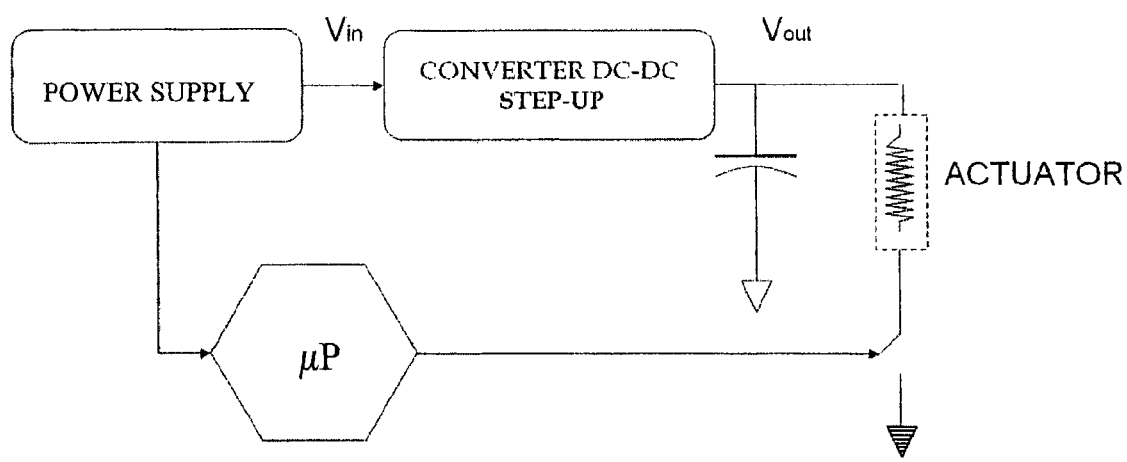
FIG. 8 is a block diagram illustrating the system of actuation of the legs.

As shown in FIG. 8, the driver is composed of a step-up DC_DC converter required to increase the $V_{in}$ of the battery by at least 8 times its value (the commercial components which can be used for this purpose are MAX668-669 from MAXIM or similar). The $V_{out}$ of the step-up charges a capacitor. The actuator is energised by discharging the capacitor for a period of time equal to a few milliseconds on the same actuator. Activation of discharging of the capacitor is generated by the microcontroller through the closure of the switch shown in FIG. 8.

For the external control of the movements and of the functions of the endoscopic capsule, in the present embodiment of the invention a man-machine interface has been developed in Visual Basic through which all the instructions necessary for movement of the legs can be sent by telemetering, while exploration instructions are pre-programmed on the microcontroller on board the capsule. Naturally other equivalent known types of interface can be used as an alternative.

In a practical embodiment of the invention a capsule was made, approximately 17 mm in diameter and 30 mm in length with legs of approximately 15 mm in length. In a prototype wires in SMA were used for actuating the legs with diameter of 75 microns. The consumption of the capsule for an inspection of the entire gastrointestinal tract, assumed to be roughly equal to 8 metres, was compatible with latest-generation batteries whose energy stored in them is of the order of 2 Wh/cc.

The endoscopic capsule according to the invention, has, compared to known endoscopic capsules, a number of advantages, including:
  the ability to move forwards, turn back and turn around on the basis of the diagnostic needs identified by the member of the medical staff;
  the ability to stop, contrasting the peristaltic forward forces, thanks to the microhooks with which the legs are equipped or the simple radial outward bending of the same legs;
  dimensional adaptability to the various gastrointestinal areas;
  greater safety compared to semi-autonomous endoscopes with inchworm locomotion, and also traditional endoscopes, which slide on the tissue without the possibility of avoiding lesions or pathologic sites. With a legged endoscopic capsule improved control of the trajectory is possible and the capsule can pass through critical areas without touching them. In fact the positioning of the legs can be accurately controlled by exploiting the transmitted visual information as a guide;
  better movement controllability in terms of length of the step, frequency, trajectory and accuracy and improved adaptability to the anatomical and biomechanical features of the environment in which it has to operate;
  greater speed of locomotion in that the legs can act as a system of amplification of the movements of the microactuators for actuation of the same, thus generating a higher overall speed;
  greater convenience of use, in that the patient is not required to wear systems for the generation of fields of force and reduction of the possible risks associated therewith.

The endoscopic capsule according to the invention can advantageously be coated with a biocompatible and biodegradable layer which avoids accidental outward bending of the legs in the mouth, making the process of swallowing easier. When the capsule reaches the stomach the coating can then be destroyed, allowing the possibility of movement of the legs. In the exploration of areas of small dimensions, such as the small intestine, with an average span of 2 cm, the capsule can proceed with the legs semi-bent, while in areas of greater gauge, such as the colon, with approximately 5 cm of diameter, the capsule can proceed with the legs almost completely extended.

The number of legs with which the capsule can be equipped depends on the speed which is to be reached and the complexity of the single step of locomotion.

Various changes and modifications to the invention may be clear on the basis of the present description. These changes and additions are understood to come within the scope and spirit of the invention, as set forth in the following claims.

The invention claimed is:

1. A teleoperated endoscopic capsule for diagnostic and therapeutic purposes inside a human body cavity, comprising: a body with a plurality of locomotion modules placed on its surface, suitable for moving said body in said cavity, a source of energy inside said body, a microcontroller in said body to actuate said locomotion modules on the basis of commands teletransmitted by an operator, a video camera for capturing images, controlled by said microcontroller, a transceiver system for receiving commands teletransmitted by the operator and for transmitting the images captured via said video camera and wherein each of said locomotion modules comprises a leg brought into contact with a wall of said cavity for transmitting a locomotion force and for moving points of contact of said leg to produce locomotion, and wherein the leg further comprises grasping means for increasing adherence of contact against said wall including a plurality of microhooks aligned along an enlarged end of said leg, said microhooks being turned towards a rear end of said body.

2. An endoscopic capsule according to claim 1, wherein said leg has at least two degrees of freedom, and means for actuating movements of said leg controlled by said microcontroller.

3. An endoscopic capsule according to claim 1, wherein said body has a front end and the rear end spaced longitudinally, and said leg has at least one degree of freedom active in a longitudinal direction of said body controlled by said actuator means.

4. An endoscopic capsule according to claim 3, wherein said leg has at least one passive degree of freedom to adapt a force of contact against said wall to deformability of said wall.

5. An endoscopic capsule according to claim 1, wherein said leg is a substantially rod-shaped element in two portions, with ends thereof connected by a knee portion with increased flexibility.

6. An endoscopic capsule according to claim 5, wherein said knee portion with increased flexibility is made by material removal.

7. An endoscopic capsule according to claim 5, wherein said knee portion with increased flexibility comprises end-of-stroke stops to limit angular movement of said knee portion.

8. An endoscopic capsule according to claim 1, wherein said leg is a substantially rod-shaped element with a plurality of sections with increased flexibility along its length.

9. An endoscopic capsule according to claim 1, wherein said microhooks extend along one edge of said leg.

10. An endoscopic capsule according to claim 1, wherein said leg is made of shape memory alloy (SMA).

11. An endoscopic capsule according to claim 1, further comprising an actuator means having a pair of wires made of shape memory alloy (SMA) connected to said leg and acting in opposition to move said leg angularly around an axis perpendicular to a longitudinal direction of said body, said wires being selectively fed with an electrical current under the control of said microcontroller.

12. An endoscopic capsule according to claim 11, wherein each locomotion module comprises a support housed longitudinally on said body, said support having a pulley located at one end of said support and an axis perpendicular to a longitudinal direction of said body, said leg extending radially from said pulley, said SMA wires being connected to said pulley at diametrically opposite ends thereof and to electrical contacts on said support.

13. An endoscopic capsule according to claim 1, wherein said locomotion modules are placed one alongside the other on said body so corresponding legs are located alternatively on a side of a front end, and on a rear end said body.

14. An endoscopic capsule according to claim 1, wherein there are at least six of said locomotion modules.

15. An endoscopic capsule according to claim 1, further-comprising actuator means for transmitting angular movements of said leg between a rest position wherein the leg is placed longitudinally along said body, and another position of maximum radial extension.

16. An endoscopic capsule according to claim 15, wherein in said rest position, said leg is housed in a support of one of said locomotion modules.

17. An endoscopic capsule according to claim 15, wherein the position of maximum radial extension of said leg is at 120° in relation to said rest position.

18. An endoscopic capsule according to claim 1, wherein a biodegradable coating is provided on said body for containing the legs during a swallowing process.

19. A system for diagnostic and therapeutic endoscopy inside a human body cavity, characterised in that it comprises an endoscopic capsule according to claim 1 and an external control interface for transmitting to said capsule the commands for its locomotion in said cavity and for the reception and processing of the obtained data.

* * * * *